(12) United States Patent
Pohl et al.

(10) Patent No.: US 11,485,990 B2
(45) Date of Patent: Nov. 1, 2022

(54) PROCESS FOR OBTAINING A CONCENTRATED PROTEIN-RICH PHASE FROM WASTE PRODUCTS OF BIOETHANOL PRODUCTION

(71) Applicant: VERBIO VEREINIGTE BIOENERGIE AG, Zörbig (DE)

(72) Inventors: Julia Pohl, Dessau-Roßlau (DE); Jan Kühling, Halle (DE); Michael Schlimbach, Halle (DE); Wolfram Klein, Leipzig (DE); Oliver Lüdtke, Markkleeberg (DE); Anne Lamp, Hamburg (DE)

(73) Assignee: VERBIO VEREINIGTE BIOENERGIE AG, Zörbig (DE)

( * ) Notice: Subject to any disclaimer, the term of this patent is extended or adjusted under 35 U.S.C. 154(b) by 221 days.

(21) Appl. No.: 16/912,562

(22) Filed: Jun. 25, 2020

(65) Prior Publication Data

US 2021/0002686 A1    Jan. 7, 2021

(30) Foreign Application Priority Data

Jul. 3, 2019  (DE) .......................... 102019004704.4

(51) Int. Cl.
| | | |
|---|---|---|
| *C12P 21/00* | (2006.01) | |
| *B01D 3/00* | (2006.01) | |
| *B01D 3/14* | (2006.01) | |

(52) U.S. Cl.
CPC .............. *C12P 21/00* (2013.01); *B01D 3/001* (2013.01); *B01D 3/143* (2013.01); *C12P 2201/00* (2013.01)

(58) Field of Classification Search
CPC .............................. B01D 3/143; C12P 2201/00
See application file for complete search history.

(56) References Cited

U.S. PATENT DOCUMENTS

| | | | |
|---|---|---|---|
| 7,829,680 B1 * | 11/2010 | Sander ..................... | C07K 1/30 530/413 |
| 8,778,433 B2 † | 7/2014 | Lee | |
| 9,516,891 B1 | 12/2016 | Roa-Espinosa | |
| 9,714,267 B2 | 7/2017 | Emanuele et al. | |
| 2015/0305370 A1 | 10/2015 | Bleyer et al. | |

FOREIGN PATENT DOCUMENTS

| | | |
|---|---|---|
| EP | 2 481 293 A1 | 8/2012 |
| EP | 2 699 655 A1 | 2/2014 |
| EP | 2 741 615 A2 | 6/2014 |
| EP | 2 847 341 A1 | 3/2015 |
| EP | 2 864 460 A1 | 4/2015 |
| EP | 2 874 503 A1 | 5/2015 |
| WO | WO0238787 A2 | 5/2002 |
| WO | WO 2012/145230 A1 | 10/2012 |
| WO | WO 2013/021161 A2 | 2/2013 |
| WO | WO 2013/170034 A1 | 11/2013 |
| WO | WO 2013/192391 A1 | 12/2013 |
| WO | WO 2014/014682 A1 | 1/2014 |
| WO | WO 2016/019374 A2 | 2/2016 |

OTHER PUBLICATIONS

Extended European Search Report dated Dec. 11, 2020, issued in EP20183458.7, 5 pages.

* cited by examiner
† cited by third party

*Primary Examiner* — Maryam Monshipouri
(74) *Attorney, Agent, or Firm* — Lewis Roca Rothgerber Christie LLP (57) ABSTRACT

1) A method for obtaining a concentrated protein-rich phase from residues of bioethanol production.

2.1) Previously, the separation of a protein-rich phase from whole stillage from bioethanol production has been achieved either by the addition of chemicals or by process steps that are complex in terms of equipment and/or energy.

2.2) Whole stillage from bioethanol production is fed to a solid-liquid separation, and the liquid phase (thin stillage) resulting from this is partially returned to the mashing process. This recirculation increases the raw protein content in the process. Part of the thin stillage is diluted and fed to a simple separation process without the addition of chemicals and temperature treatment, with a protein-rich phase being obtained.

2.3) A protein-rich phase is obtained from residues of bioethanol production.

15 Claims, 3 Drawing Sheets

PROCESS FOR OBTAINING A CONCENTRATED PROTEIN-RICH PHASE FROM WASTE PRODUCTS OF BIOETHANOL PRODUCTION

CROSS-REFERENCE TO RELATED APPLICATION(S)

This application claims priority of German Patent Application Number 102019004704.4, filed on Jul. 3, 2019, the entire contents of which are incorporated herein by reference.

Definitions

The term "mashing" describes the process of adding liquid to cereal meal, wherein the liquid is a mixture of process liquids and possibly water.

In this invention, the term "thin stillage" comprises the liquid phase produced by a solid-liquid separation of the whole stillage.

In the context of this invention, "dissolved DM content" is understood to mean the dry matter which is present in dissolved form in the filtrate after centrifugation and fine filtration (pore size 0.2. μm) of a diluted starting sample, such as whole stillage. The dissolved DM content is given in wt %.

The term "cold mashing process" means the pressureless enzymatic breakdown of the mashed-in cereal meal at a temperature below the gelatinisation temperature of the starch, preferably in the range between 45° C. and 66° C. In this process, the starch molecules and the starch-enveloping proteins are broken down and in some cases the starch is saccharified.

The term "clear phase" in this invention refers to the aqueous phase resulting from the separation of the diluted thin stillage.

The term "concentrate" refers to the protein-rich phase produced from the diluted thin stillage.

In this invention, the term "process liquid" comprises all liquids containing solids as well as all liquids free of solids that are produced in the process.

In this invention "raw protein content" means the proportion of raw protein in the dry matter. It is expressed in % DM (w/w).

In this invention, the term "whole stillage" comprises the residue from the distillation of an ethanol-containing cereal mash.

Within this invention, the term "spent grains" describes the solid phase which is separated from the whole stillage by a solid-liquid separation.

The "separation grain size" describes the particle size which, after the separation of an initial sample comprising different particle size fractions, such as whole stillage, is present at a level of 50% in each of the coarse phase, such as spent grains, and the fine phase, such as thin stillage.

The term "inflow" refers to the diluted thin stillage which is separated into clear phase and concentrate.

PRIOR ART

The production of bioethanol from plant raw materials is known. In Germany, the amount of bioethanol produced has more than doubled in the last 10 years. The trend for the future is positive, as a further reduction in $CO_2$ emissions from fuels is required by law in the coming years and can be achieved by incorporating bioethanol. From a global perspective, small-grained cereal types such as rye, wheat and triticale are one of the main raw materials for bioethanol production, along with maize.

For bioethanol production, the cereal is ground, mashed and fermented with the addition of yeast. The fermented mash is fed to a distillation process, in which the separation of the ethanol produces what is known as the whole stillage, which consists of components, salts and yeast that have not been converted to ethanol. As a rule, the whole stillage is subjected to a solid-liquid separation process in which the solid cereal residues are separated from the liquid phase, known as the thin stillage. The separated solids are often referred to as spent grains. Thin stillage and spent grains are used in different variants, individually or in combination, mainly as animal feed.

A known and, especially in the USA, widely used animal feed is what is known as DDGS (Dried Distillers Grains with Solubles), which consists of dried spent grains and dried thin stillage concentrate and has a dry matter content of approximately 90%. The drying process concentrates the contained nutrients in comparison to the liquid whole stillage, resulting in a higher-quality feed.

The condensate produced during drying or evaporation is recirculated to the mashing process so that the fresh water requirement is reduced or completely covered.

The raw protein content in DDGS is about 30% DM, i.e. with a DM content of 90% the raw protein makes up 27% of the original substance. In comparison, liquid whole stillage contains only about 2-4% raw protein in relation to the original substance. Due to the high fibre content in DDGS, however, this feed may only be fed to ruminants.

The raw protein content is an essential criterion in the assessment of a feed. The higher the raw protein content, the more valuable the feed is. For this reason, an increase in the raw protein content is sought in order to upgrade a feed. At the same time, the fibre content should be minimal so that the use of the feed is not restricted to ruminants.

Various methods for the separation of proteins from whole stillage or for the enrichment of proteins in individual whole stillage fractions are known to a person skilled in the art.

A possible variant for the recovery of proteins from whole stillage is the extraction of these. EP2874503 A1 describes a method for the extraction of proteins from spent grains with ethanol. For this purpose the spent grains are diluted volumetrically with 50% ethanol. After a residence time of approximately 20 min at approximately 49° C. the solid is separated from the protein-containing solvent. To isolate the proteins, the solvent must then be removed.

On the one hand, this method is disadvantageous because only the small amount of proteins contained in the spent grains is separated and the proteins in the thin stillage are not taken into account. On the other hand, the high demand for ethanol and the additional step to remove the ethanol have a negative effect on the costs of the process.

A further method, in which protein separation is carried out with the addition of a chemical, is part of the complex process for processing whole stillage described in patent U.S. Pat. No. 9,516,891 B1. In that case, thin stillage is mixed with cationic and anionic copolymers, such as acrylamide-acrylic acid copolymers, which cause flocculation of the proteins. The flocculated proteins can then be separated with the aid of a tricanter.

The disadvantages here are the costs for the flocculant and the limited usability of the protein product due to the flocculant contained. It is not clear from the patent whether and how the flocculant is separated from the proteins again, and consequently the product cannot be used as feed without further treatment.

Methods for protein separation from whole stillage which do not require the addition of chemicals and flocculants are most suitable in respect of the applicability of the product as feed. In this case, the protein product does not contain any chemical impurities, and no additional process step is required to separate the chemicals.

The method described in WO2016019374 A2 involves a temperature treatment of the whole stillage in the range of 93° C. to 177° C. for a period of 3 min to 180 min. This temperature treatment denatures the proteins and forms agglomerates which can be separated more easily, for example by gravity sedimentation or centrifugation.

A major disadvantage here is the high energy requirement for the temperature treatment of the whole stillage.

EP2481293 B1 discloses a temperature-saving method for producing a protein-containing product from thin stillage (DM content approximately 4%), in which the thin stillage is concentrated in a filtration plant, for example an ultrafiltration plant. A partial flow of the retentate from the filtration plant is recirculated to the receiver tank for the filtration in order to set a DM content of approximately 7% for the optimum operating point of the filtration plant. Optionally, a temperature-saving drying and pelleting of the protein product may follow at the end.

The high equipment and operational expenditure due to the filtration system must be seen as a disadvantage here.

A person skilled in the art is aware that disc centrifuges are often used for the separation of proteins from thin stillage. Corresponding examples can be found in EP2699655 A1 and EP2741615 A2, among others.

If not all of the thin stillage is to be processed into dried feed or if the plant concept does not generally provide for drying of the thin stillage, the need for fresh water can be reduced by recirculating at least part of the thin stillage to the mashing process. However, the recirculatable portion is limited by several factors or requires special treatment.

In EP2864460 A1 it is described that when the thin stillage is recirculated, the contained proteins and nutrients have a positive effect on the fermentation, but the far greater negative aspect is the contained suspended DM. This limits the amount of fresh meal that can be added to the mash. The viscosity also increases, which impairs pumpability. As an alternative, therefore, after temperature treatment of the thin stillage (93° C. 177° C., 3-180 min), an aqueous fraction is separated from the thin stillage in a further separation process, which aqueous fraction is known as the stick water, which contains less than 1% suspended DM and is more suitable for recirculation. However, this process is very complex in terms of equipment and energy-intensive.

Part of the process revealed in EP2847341 A1 is the recirculation of thin stillage (DM approximately 10%) or whole stillage (DM approximately 16%) up to a proportion of 45% into the mash. Before fermentation, the mash is subjected to jet cooking, i.e. high-temperature digestion (100° C.-150° C.) under pressure (3 bar 5 bar) to liquefy the starch and reduce viscosity. The disadvantages here are the high costs for the equipment and the high energy demand.

At present, no methods are known in which a targeted enrichment of the proteins in the mash and consequently in the whole stillage is achieved by recirculating the whole stillage to the mashing process. By enriching the proteins, their separation is simplified and the value of the product produced is elevated due to an increased raw protein content. The recirculation of significant amounts of whole stillage without an additional energy-intensive treatment step in an economical production process is also not described.

Problem and Solution

The problem addressed by the invention is therefore to selectively enrich the proteins in an efficient fermentation process that conserves energy and resources, to separate them in a simple and cost-effective manner, and to produce a protein product with higher value and improved marketability.

The problem is solved by a method for obtaining a concentrated protein-rich phase from residues of bioethanol production, comprising the following steps:

a. the ground cereal is mashed before fermentation b. the fermented mash is fed to a distillation process which produces whole stillage as residue c. the whole stillage from b) is fed to a solid-liquid separation and the resulting solid is discharged from the process d. the liquid phase from c), the thin stillage, is partially returned to the mashing process, with at least 0.15 kg thin stillage DM per kg of cereal DM being returned and the raw protein content being increased by the recirculation of the thin stillage to the mashing process e. at least part of the liquid phase from c) is diluted with an aqueous process liquid and fed to a further separation process, the aqueous phase separated in this process, the clear phase, containing predominantly the dissolved dry matter, and the concentrated phase produced, the concentrate, containing predominantly the protein-rich suspended dry matter.

The advantages achieved with this invention consist in particular in the fact that, due to the process conditions (low pH value, low temperatures), the proteins are present as small particles in the thin stillage and are enriched by the partial recirculation of the thin stillage to the mashing process, whereby the raw protein content is significantly increased and the proteins can be easily separated without the addition of chemicals and without an energy-intensive treatment step.

To solve this problem, the invention provides a method according to claim 1. Advantageous refinements are mentioned in the dependent claims. The wording of all claims is provided by reference to the content of the description.

In a preferred embodiment, the method according to the invention is designed in such a way that the cereal is fed to a dry grinding.

In a further preferred embodiment, the method according to the invention is designed in such a way that a cold mashing process precedes the fermentation.

In a further preferred embodiment, the method according to the invention is designed in such a way that mashing is preferably carried out with at least 0.25 kg thin stillage DM per kg of cereal DM and particularly preferably with at least 0.35 kg thin stillage DM per kg of cereal DM.

In a further preferred embodiment, the method according to the invention is designed in such a way that, by the partial recirculation to the mashing process, the raw protein content of the thin stillage is increased by at least 5% rel. and preferably by at least 10% rel. compared to the raw protein content of the cereal less starch.

In another preferred embodiment, the method according to the invention is designed in such a way that a pH value<4.0 is maintained throughout the entire process.

In a further preferred embodiment, the method according to the invention is designed in such a way that, due to the special mode of operation, i.e. the recirculation of significant amounts of thin stillage into the mashing process and thus the multiple passes through the distillery, the predominant proportion of particles in the thin stillage has a size smaller than 50 µm.

In another preferred embodiment, the method according to the invention is designed in such a way that the thin stillage has a DM content of at least 8%.

In a further preferred embodiment, the method according to the invention is designed in such a way that, by the targeted use of enzymes, for example cellulases, hemicellulases, trehalases, xylanases, amylases, lipases, phytases and/or combinations thereof, non-protein-containing suspended substances are cleaved and dissolved.

In another preferred embodiment, the method according to the invention is designed in such a way that the solid-liquid separation of the whole stillage takes place in a filter press or in a decanter.

In another preferred embodiment, the method according to the invention is designed in such a way that the separation grain size in the solid-liquid separation of the whole stillage is in the range 150-500 µm, preferably 200-300 µm.

In another preferred embodiment, the method according to the invention is designed in such a way that the thin stillage is exposed to a maximum temperature of 90° C. throughout the entire process.

In another preferred embodiment, the method according to the invention is designed in such a way that the thin stillage can be fed, prior to the separation process, to an enzymatic treatment for the cleavage of non-protein-containing suspended substances.

In another preferred embodiment, the process according to the invention is designed in such a way that the partial dilution of the thin stillage is carried out with a suitable process liquid, such as condensate from the thin stillage evaporation.

In a further preferred embodiment, the method according to the invention is designed in such a way that the thin stillage is diluted with a suitable process liquid in a ratio of 1:5, preferably 1:3 and particularly preferably 1:1 before separation.

In another preferred embodiment, the method according to the invention is designed in such a way that the inflow is fed to a pre-cleaning process before the separation step.

In another preferred embodiment, the method according to the invention is designed in such a way that the pre-cleaning of the inflow is carried out with the aid of a rotary brush screen or a wire wedge filter.

In a further preferred embodiment, the method according to the invention is designed in such a way that the separation of the diluted thin stillage into clear phase and concentrate with the aid of a separator takes place at least at 2800×g, preferably at least 3500×g and particularly preferably at least 5000×g.

In another preferred embodiment, the method according to the invention is designed in such a way that the concentrate has a raw protein content increased by at least 15% rel. compared to thin stillage.

In a further preferred embodiment, the method according to the invention is designed in such a way that the concentrate has a raw protein content of at least 44% DM and preferably at least 48% DM.

In a further preferred embodiment, the method according to the invention is designed in such a way that a maximum of ⅓ of the DM in the concentrate is present in dissolved form.

In another preferred embodiment, the method according to the invention is designed in such a way that the clear phase is at least partially returned to the process, for example into the thin stillage evaporation.

In another preferred embodiment, the method according to the invention is designed in such a way that the clear phase can be fed at least partially to an ultrafiltration unit to increase the protein yield.

In another preferred embodiment, the method according to the invention is designed in such a way that the concentrate is at least partially used directly as a high-quality protein feed or is fed to further treatment steps.

In another preferred embodiment, the method according to the invention is designed in such a way that the concentrate can be fed to an enzymatic treatment with subsequent solid-liquid separation to increase the raw protein content.

The method according to the invention also applies in particular to all combinations of the preferred embodiments described above.

Description of the Solution

The raw protein content depends on the type of cereal. It amounts to approximately 10-15% DM in small-grained cereals such as wheat, rye, triticale and barley and approximately 9% DM in maize. Cereal grains are principally composed of husk, endosperm and germ. The proteins contained in cereal grains are mainly found in the endosperm, which contains about 70% of the proteins. This applies to wheat and rye as well as to maize. In the case of the small-grained cereals, approximately 10% of the proteins are present in the germ, whereas in maize it is approximately 20%, since the maize germ is considerably larger. The remaining proteins are distributed among the remaining components.

When cereal is processed into bioethanol, the proteins it contains are not broken down by the yeast during fermentation, but are retained. The complete conversion of starch to ethanol would result in a concentration of the raw protein content by a factor of about 3 compared to the starting material. Furthermore, the yeast cells themselves also contain and produce proteins. At the end of the fermentation or after the separation of the produced ethanol from the mash, the whole stillage thus contains cereal and yeast proteins.

As a rule, whole stillage has a DM content of at least 10% and a raw protein content of at least approximately 25% DM. The DM content is composed of suspended and dissolved fractions, which are present in approximately the same ratio.

It is known to a person skilled in the art that the whole stillage is at least partially subjected to a solid-liquid separation in order to feed the thin stillage to an evaporation or drying process. The separated solids, often referred to as spent grains, due to the high fibre content are mainly used as cattle feed, either untreated or dried.

It is desirable to produce a competitive, protein-rich, low-fibre product from the whole stillage in a cost-effective, simple and efficient method, which product, due to the higher nutritional value, has a higher value and may be more widely used.

Surprisingly, it has been found that a recirculation of significant amounts of thin stillage in combination with the cold mashing process can be economically implemented. For mashing, at least 0.15 kg, preferably at least 0.25 kg and particularly preferably at least 0.35 kg of thin stillage DM per kg of cereal DM is returned. This mode of operation results in ethanol contents in the fermented mash in the range 5-8 wt %. Previously, it was known that such a high recirculation is implementable only in combination with jet cooking.

Figure 1:
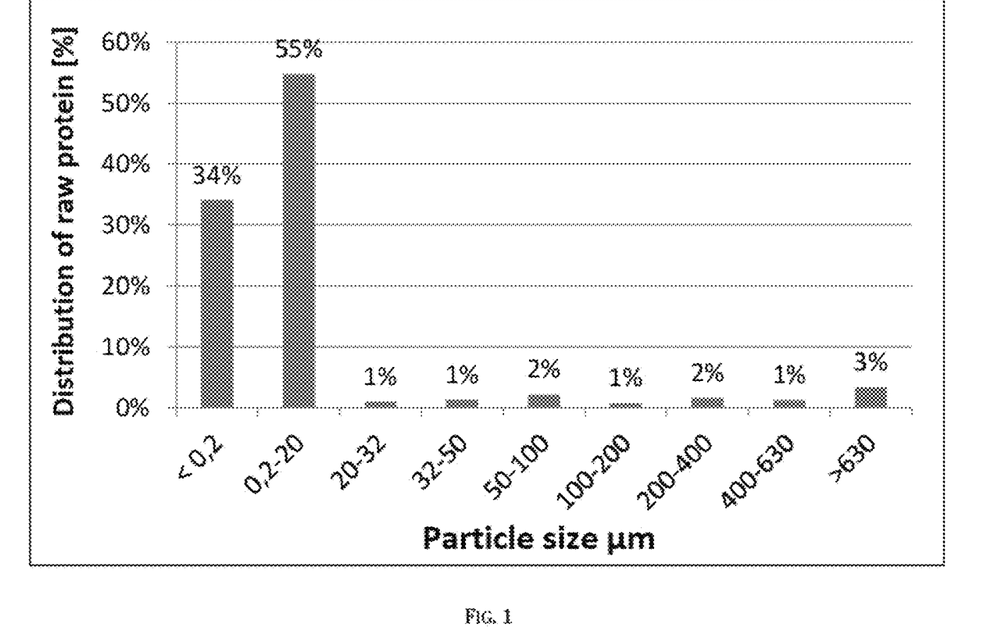
FIG. 1 SHOWS THE DISTRIBUTION OF THE RAW PROTEIN IN THE INDIVIDUAL PARTICLE SIZE FRACTIONS USING THE EXAMPLE OF A WHOLE STILLAGE FROM THE PRESENT PROCESS

Furthermore, it has been found that the main potential for producing a protein-rich product lies in the thin stillage, since more than 70% of the raw protein in the whole stillage is contained in particles smaller than 50 μm and at least 70% of these particles remain in the thin stillage during solid-liquid separation. FIG. 1 shows the distribution of the raw protein in the individual particle size fractions using the example of a whole stillage from the present process. In this example the particles<50 μm contain approximately 90% of the raw protein. The proportion of proteins separated with the spent grains is therefore low.

Through the combination of solid-liquid separation and high thin stillage recirculation, the protein-rich particles are enriched, which significantly increases the raw protein content.

In addition, the high level of recirculation results in a considerable reduction in the amount of fresh water required, making the process more efficient and conserving resources. The total fresh water requirement can be reduced to a minimum or completely covered by returning other process liquids, for example condensate from thin stillage evaporation or lutter water from the distillation, partially back into the mashing process.

A comparison of the particle sizes of the whole stillage from the present process with those of a whole stillage from an external bioethanol production plant shows that the particles in the whole stillage of the described process are significantly smaller (Tab. 1). On average, these particles are only about half as large as those in the external whole stillage. It is also clear that the thin stillage of the present process predominantly contains only very small particles, since 50% of the particles are ≤10 μm (D10). These small particle sizes are a clear indication that the special mode of operation, i.e. the recirculation of significant amounts of thin stillage to the mashing process and thus the multiple passes through the distillery, reduces the particle sizes.

TABLE 1

|  | External whole stillage | Whole stillage | Thin stillage |
| --- | --- | --- | --- |
| Average value [μm]. | 485.7 | 260.0 | 37.0 |
| D10 [μm] | 10.3 | 6.2 | 4.6 |
| D50 [μm] | 412.2 | 60.7 | 10 |
| D90 [μm] | 1188.8 | 783.3 | 119.3 |

The invention is explained below on the basis of the recovery of a concentrated protein-rich phase from whole stillages of bioethanol production.

Cereals, such as rye, wheat, triticale, barley, maize and/or combinations thereof, are dry-ground and processed into bioethanol in an efficient fermentation process that conserves energy and resources. The ground cereal is mashed in with a mixture of process liquids. In case that the available process liquids are not sufficient and/or contain substances that interfere with the fermentation, for example acetic acid in increased concentration, additional water is added to the mashing process. The mashed-in cereal meal is broken down during the cold mashing process, i.e. below the gelatinisation temperature of the starch, preferably between 45° C. and 66° C. These low temperatures are particularly advantageous due to the low energy requirement.

By adding enzymes in the ethanol process, such as cellulases, amylases, trehalases, phytases, hemicellulases, lipases and/or combinations thereof, non-protein-containing substances are cleaved and dissolved and thus transferred from the suspended to the dissolved fraction, which is then separated selectively during the further course of the process.

Until distillation, a temperature of 66° C. is not exceeded and in the further course of the process a maximum of 90° C. is reached for a limited time. The pH value is constantly <4.0.

Due to the low pH value, the low temperatures and the resulting partial denaturation, the proteins are present as small particles which remain in the thin stillage during the solid-liquid separation of the whole stillage, thus allowing a targeted protein enrichment in the process by the partial thin stillage recirculation. The low pH value also means that small proteins are predominantly present in undissolved form and can therefore be separated more easily. A particular advantage of this method, due to the low temperatures, is the particularly low energy requirement of the process.

After separation of the ethanol produced from the mash, the whole stillage is at least partially fed to a solid-liquid separation process. A decanter or filter press, for example, is used for this separation. The separation particle size in this separation process is in the range of 150-500 μm, preferably 200-300 μm. The separated solids, which contain a maximum of 15% of the total raw protein, are discharged and used as feed, mainly for cattle.

The thin stillage produced has a DM content of at least 8% and a raw protein content of at least 30% DM. The proportions of dissolved and suspended dry matter are approximately equal. At least 70% of the total raw protein of the thin stillage is contained in the particles<50 μm and thus in the suspended DM.

It is particularly advantageous to carry out mashing with a significant thin stillage content, i.e. at least 0.15 kg, preferably at least 0.25 kg and particularly preferably at least 0.35 kg thin stillage DM per kg of cereal DM, which results in an enrichment of the small, protein-rich particles. After several cycles with the described thin stillage recirculation, the concentration of these particles reaches a constant value. The raw protein content of the thin stillage increases significantly by at least 5% rel. compared to the cereal less starch, i.e. compared to the raw protein content which would result after complete conversion of the starch, and is kept constant at this level with the same recirculation.

Figure 2:
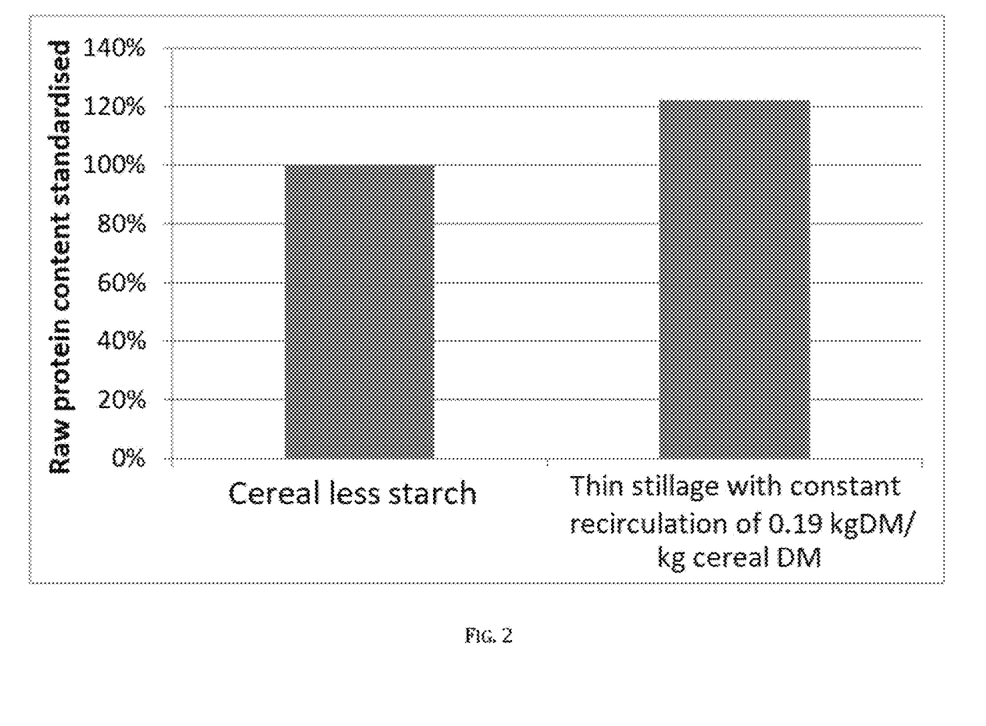
FIG. 2 SHOWS AN EXAMPLE OF STANDARDISED RAW PROTEIN CONTENT OF CEREAL LESS STARCH AND OF A THIN STILLAGE WITH A CONSTANT RECIRCULATION OF 0.19 KG THIN STILLAGE DM/KG CEREAL DM (STANDARDISED TO RAW PROTEIN CONTENT OF CEREAL LESS STARCH)

FIG. 2 shows an example in which, with a constant recirculation of 0.19 kg of thin stillage DM per kg of cereal DM in the mashing process, the raw protein content in the thin stillage is increased by approximately 20% rel. compared to the raw protein content in the cereal less starch.

Before the thin stillage is subjected to separation, an enzymatic treatment of at least part of the thin stillage with cellulases, hemicellulases, lipases and/or amylases or combinations thereof may be carried out to cleave undissolved non-protein-containing substances and transfer them to the dissolved fraction, thereby additionally increasing the raw protein content of the suspended DM.

In a particularly efficient process, the enzymatic treatment takes place directly under the conditions (temperature, pH) present in the thin stillage. Alternatively, the pH value of the thin stillage can be adjusted to an optimal value for the enzymes by adding lye, such as NaOH, KOH or $NH_4HCO_3$, in order to ensure optimal enzyme activity. The temperature can also be adjusted to the requirements of the enzymes. The simultaneous adjustment of pH and temperature is advantageous.

To obtain a protein-rich phase from at least part of the thin stillage, it is advantageous to dilute it with an aqueous process liquid before the separation step. On the one hand, this results in a reduction of the viscosity. On the other hand the dilution causes a reduction of the content of dissolved DM and thus of the salt content, such as sulphate. Most suitable is an aqueous process liquid which contains almost no dissolved DM.

Such an aqueous process liquid originates, for example, from thin stillage evaporation, in which a thin stillage concentrate is produced from at least part of the thin stillage produced, which concentrate has a DM content approximately twice as high as the starting material.

This process liquid is particularly advantageous because it has a temperature similar to the thin stillage itself, so that a temperature of approximately 50° C. is reached during dilution, which also has a positive effect on the viscosity and thus on the subsequent separation. The process liquids can therefore be used energetically efficiently with their reached temperature without the need for temperature control.

The thin stillage should preferably be diluted in a ratio of 1:5, preferably 1:3 and particularly preferably 1:1. In principle, the more the thin stillage is diluted, the easier it is to separate the suspended protein-rich particles in the following separation process. However, the proportion of thin stillage must be so large that significant amounts of suspended DM can be separated. The dilution should therefore be chosen so that the process is economically feasible.

To ensure optimal separation, the diluted thin stillage, called the inflow, should be subjected to a pre-cleaning process to remove any coarse particles and foreign matter that might still be present and that would impair separation or contaminate the protein product. The pre-cleaning can take place, for example, in the form of a solid-liquid separation using a coarse filter.

A separator is used to separate the inflow. In this step the suspended DM accumulates in the concentrated phase, referred to as concentrate, whereas the dissolved DM is mainly discharged via the aqueous phase, or what is known as the clear phase.

One way to optimise the separation is to control the temperature of the inflow stream to temperatures in the range of 50° C. 90° C., which reduces viscosity and allows a smaller separation particle size to be achieved. The smaller the separation particle size, the fewer protein-rich particles are separated with the clear phase. Whether temperature control>50° C. is expedient must be evaluated on the basis of the protein yield and the necessary energy requirement.

Multi-stage separation is also possible and advantageous in order to increase the raw protein content and reduce the salt content. For this purpose, the concentrate is diluted again with an aqueous process liquid, for example condensate from thin stillage evaporation, after the first separation step and fed to a new separation stage, for example a separator.

Optionally, the concentrate can be treated before this separation stage with enzymes, for example cellulases, hemicellulases, lipases and/or amylases or combinations thereof, in order to cleave undissolved non-protein-containing substances and transfer them into the dissolved fraction. An enzymatic treatment at this point in the process is particularly advantageous, since less enzyme is required due to the lower volume flows, and any necessary residence-time containers can be made with smaller dimensions.

In the clear phase, the proportion of dissolved DM makes up at least ⅔ of the total DM. The concentrate has a maximum dissolved DM proportion of ⅓ of the total DM, and the raw protein content is increased by at least 15% rel, compared to thin stillage.

In order to increase the efficiency of the entire process and the protein yield, it is advantageous to feed at least a proportion of the clear phase to an ultrafiltration unit in order to recover proteins still contained in it. The resulting permeate can be returned to the thin stillage evaporation.

Alternatively, the clear phase can also be subjected to evaporation or mixed with the thin stillage evaporation. The resulting condensate can be returned to the mashing process and/or used to dilute the thin stillage or concentrate in the case of multi-stage separation. A direct return of the clear phase to the mashing process is not advisable in order to avoid enrichment of the non-protein-containing dissolved solids.

The protein-rich concentrate can be used directly as a high-quality protein feed or can be fed to subsequent treatment steps for further concentration, such as evaporation or spray drying.

DETAILED DESCRIPTION OF PREFERRED EMBODIMENTS

Practical Example 1

Figure 3:
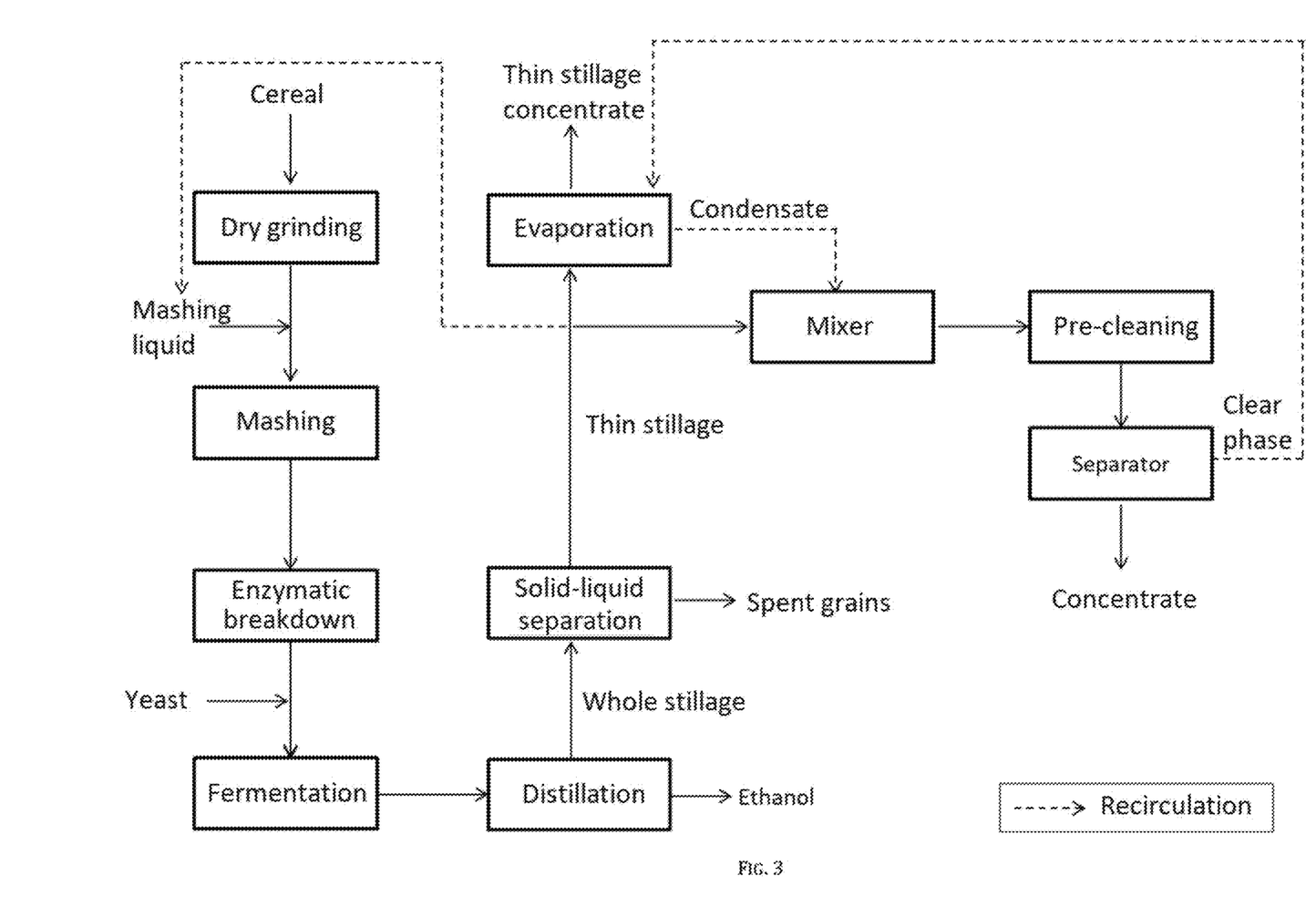
FIG. 3 SHOWS A FLOW CHART OF A POSSIBLE EMBODIMENT ACCORDING TO THE INVENTION

The possibility of a technical implementation of the method is illustrated below by the recovery of a concentrated protein-rich phase from triticale-rye thin stillage (FIG. 3).

A triticale-rye mixture contains the following ingredients:

TABLE 2

| | |
|---|---|
| Dry matter | 85% OS |
| Starch | 67% DM |
| Raw protein | 11% DM |

OS - original substance

If the starch were fully converted, the raw protein content would be 34% DM.

Before fermentation, a triticale-rye mixture is dry-ground and mixed with 0.24 kg thin stillage DM per kg of cereal DM and water in a ratio of 1:4.0, i.e. one part cereal and 4 parts liquid. The enzymatic digestion of the mash takes place at approximately 47° C. By adding the yeast the fermentation is started, which takes about 60 hours. The ethanol produced is then separated from the fermented mash in the distillation.

The resulting whole stillage is fed at a mass flow rate of approximately 71 t/h to a solid-liquid separation in a decanter. The separation particle size of the decanter is approximately 250 µm. All particles larger than 390 µm are completely separated in this step and contain 5% of the raw protein originally present in the whole stillage. About 76% of the protein-rich particles<50 µm remain in the thin stillage. The mass flow rate of the separated solids which are discharged is approximately 7 t/h; the thin stillage mass flow rate is approximately 64 t/h.

The thin stillage has a DM content of approximately 13%, of which about half is present in suspended or dissolved form. The average particle size is 38 µm; ¾ of the particles are smaller than 20 µm. The particles<20 µm contain about 90% of the raw protein.

A thin stillage mass flow rate of 31 t/h is returned to the mashing process (shown as dashed lines in FIG. 3); 19 t/h go into evaporation. The remaining thin stillage is fed into a collecting tank and from there into a stirred tank into which the condensate from the thin stillage evaporation is simultaneously fed (shown as dashed lines in FIG. 3). The thin stillage and the condensate are mixed in the ratio 1:1.

The diluted thin stillage, referred to hereinafter as the inflow, has a temperature of 50° C. and is first pre-cleaned in a rotary brush screen to separate coarse particles and impurities. The gap width of the filter screen is 0.4 mm.

With a mass flow rate of 12 t/h the pre-cleaned inflow is led to the nozzle separator. This contains 12 nozzles, which are arranged on the underside of the drum and have a diameter of 0.7 mm. Separation of the inflow in the separator takes place at approximately 5500×g, with the clear phase flowing out via the gripper in the upper part. The solids collect at the edge and are discharged through the nozzles at the underside, limiting the concentrate flow and thus ensuring enrichment.

Table 3 compares the mass flow rates, DM and raw protein contents of the individual flows of the nozzle separator. The raw protein content of the concentrate shows that the protein-rich particles could be successfully enriched under the stated process conditions. The yield of raw protein in this example is 47%.

TABLE 3

|  |  | Inflow | Clear phase | Concentrate |
|---|---|---|---|---|
| Mass flow rate | [t/h] | 12.0 | 9.8 | 2.2 |
| Dry matter content | [wt %] | 6.2 | 4.6 | 13.3 |
| Raw protein content | [% DM] | 41 | 36 | 50 |

The separated clear phase is returned to the evaporation (shown as dashed lines in FIG. 3) and the resulting condensate is again available as a dilution medium for the thin stillage. The protein-rich concentrate produced is collected and used either directly or after evaporation or spray drying as a high-quality protein feed.

Compared with animal feed currently available on the market, which has been produced from residues of bioethanol production (Table 4), the concentrate has a considerably higher value due to the significantly increased raw protein content.

TABLE 4

|  | DM [% DM] | Raw protein content [% DM]. |
|---|---|---|
| ProtiGrain ®[(1)] | 90 | 29 |
| Wheat/barley Dried Distillers Grains with Solubles [(2)] | 90 | 38 |
| Pressed whole stillage[(3)] | 34.5 | 27 |
| GrainPro[(4)] | 27 | 37 |

[(1)]http://www.cropenergies.com/de/Downloads/Broschueren/Broschueren-Dateien/Datenblatt_Protigrain/DatenblattProtiGrain_Juli_2016.pdf (retrieved 13 Mar. 2019)
[(2)] https://www.lfl.bayern.de/mam/cms07/ite/dateien/trockenschlempe_merkblatt.pdf (retrieved on 13 Mar. 2019)
[(3)]http://futtermittel-getreidetechnik.de/pages/produkte/press-schlempe.php (retrieved on 13 Mar. 2019)
[(4)]https://vantriest.eu/de/product/grain-pro-3/ (retrieved on 13 Mar. 2019)

Practical Example 2

Figure 4:
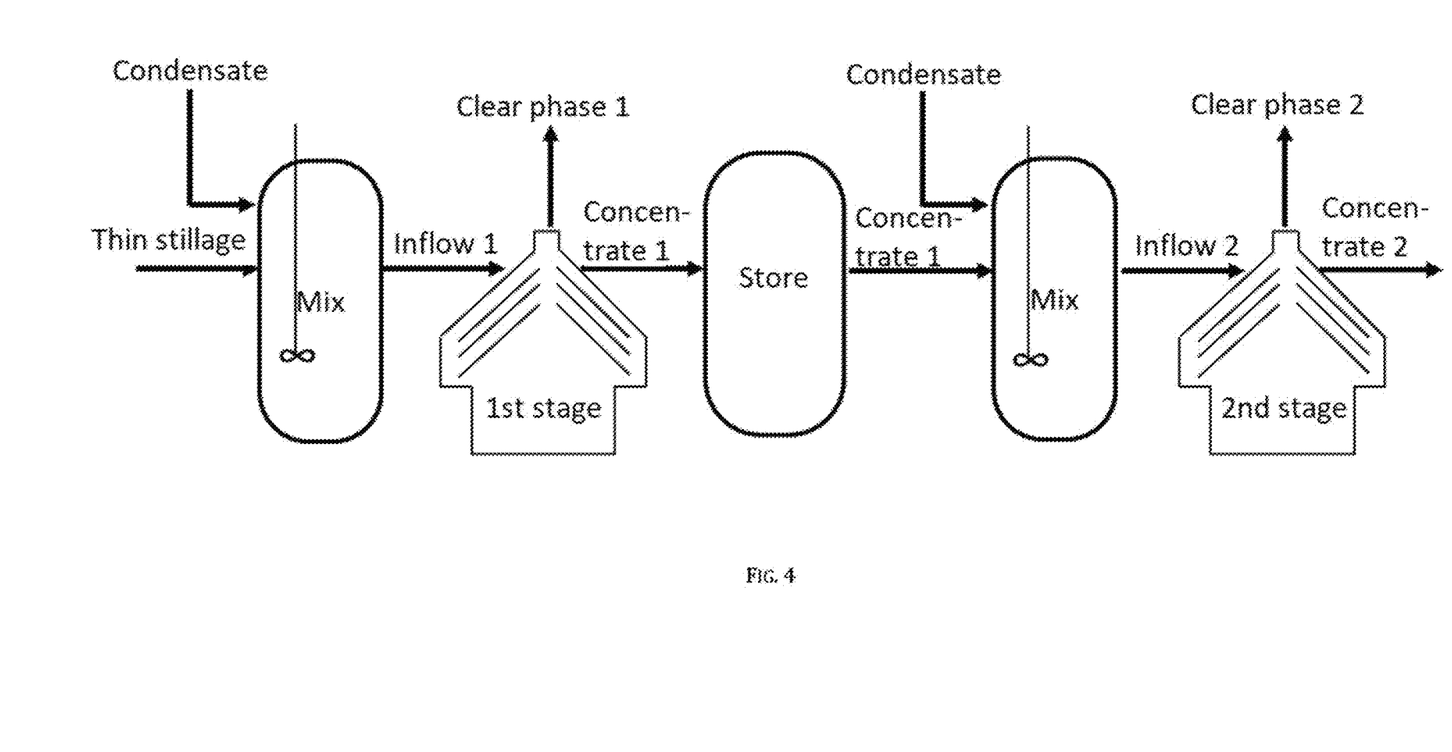
FIG. 4 SHOWS A FLOW CHART OF A POSSIBLE EMBODIMENT ACCORDING TO THE INVENTION IN THE FORM OF A TWO-STAGE SEPARATION

A further possibility of a technical implementation of the method will be illustrated hereinafter by the recovery of a concentrated protein-rich phase by a two-stage separation in a nozzle separator (FIG. 4).

Thin stillage from the ethanol process is mixed in a stirred vessel with condensate from the thin stillage evaporation in a ratio of 1:1. This stream, referred to as inflow 1, is fed to the nozzle separator with a mass flow rate of 10.8 t/h and separated at approximately 5500×g into 8.4 t/h clear phase 1 and 2.4 t/h concentrate 1.

The relevant measured quantities of the streams of the $1^{st}$ separation stage are listed in Table 5. The yield of raw protein is 50%.

TABLE 5

|  |  | Inflow 1 | Clear phase 1 | Concentrate 1 |
|---|---|---|---|---|
| Mass flow rate | [t/h] | 10.8 | 8.4 | 2.4 |
| Dry matter content | [wt %] | 8.0 | 6.2 | 14.3 |
| Raw protein content | [% DM] | 41 | 34 | 52 |

The concentrate 1 is first collected in a receiver tank, since a minimum supply to the nozzle separator is required for the $2^{nd}$ separation step. When the tank is filled, the concentrate 1 is fed into a stirred tank where it is diluted with condensate from the thin stillage evaporation in a ratio of 1:1. This stream, referred to as inflow 2, is fed to the nozzle separator at a mass flow rate of 10.8 t/h and separated at approximately 5500×g into 8.4 t/h clear phase 2 and 2.4 t/h concentrate 2. The relevant measured quantities of the streams of the $2^{nd}$ separation stage are listed in Table 6. The yield of raw protein in the $2^{nd}$ separation stage is 62%.

TABLE 6

|  |  | Inflow 2 | Clear phase 2 | Concentrate 2 |
|---|---|---|---|---|
| Mass flow rate | [t/h] | 10.8 | 8.4 | 2.4 |
| Dry matter content | [wt %] | 6.8 | 3.7 | 17.4 |
| Raw protein content | [% DM] | 53 | 47 | 58 |

The raw protein content in concentrate 2 shows that a two-stage separation results in a significant improvement of the protein product. The total yield of raw protein by a two-stage separation in this example is 31%.

Practical Example 3

A further possibility of carrying out the method on a laboratory scale is illustrated below by the recovery of a concentrated protein-rich phase starting from a concentrate that was produced as in Example 1 and then treated enzymatically.

The concentrate used has a DM content of 13.7% and a raw protein content of 48% DM. For the enzymatic treatment, 250 g of the concentrate is weighed into a 500 ml fermenting flask. The enzyme used is a preparation with cellulase, hemicellulase and xylanase activity in a dosage of 0.1% DM. In the reference batch no enzyme is added to the concentrate. The fermenting flasks are sealed with a fermentation tube and incubated in a shaker at 150 rpm and 33° C. for 72 h. At the end of the incubation period, 100 g of the treated material (from the flask with enzyme or from the flask without enzyme) are mixed with 100 g of tap water, previously temperature-controlled to 33° C., and then centrifuged at 4770×g for 15 min. The raw protein content of both pellets is determined.

For comparison, the concentrate, which served as starting material for the experiments, is temperature-controlled to 33° C. and diluted with tap water in a ratio of 1:1 as described above and centrifuged for 15 min at 4770×g. The resulting pellet is analysed.

The DM and raw protein contents of the pellets are summarised in Table 7.

TABLE 7

| | | Pellet from concentrate | Pellet from treatment without enzyme | Pellet from treatment with enzyme |
|---|---|---|---|---|
| Dry matter content | [wt %] | 25.0 | 25.2 | 24.4 |
| Raw protein content | [% DM] | 56 | 56 | 61 |

The enzymatic treatment significantly increases the raw protein content in the pellet. The DM content is reduced because the enzymes cleave and dissolve undissolved non-protein-containing substances, which remain in the supernatant after centrifugation.

The invention claimed is:

1. A method for obtaining a concentrated protein-rich phase from waste products of bioethanol production, characterised in that:
  a) a ground cereal is mashed in a mashing process to produce a mashed ground cereal before fermentation;
  b) fermented mash resulting from the fermentation of the mashed ground cereal is fed to a distillation process which produces whole stillage as waste product;
  c) the whole stillage from b) is fed to a solid-liquid separation to produce a liquid phase (thin stillage) and a solid, and the resulting solid is discharged from the method;
  d) the thin stillage is partially returned to the mashing process, with at least 0.15 kg thin stillage DM per kg of cereal DM being returned and the raw protein content of the thin stillage being increased by recirculating the thin stillage to the mashing process; and
  e) at least part of the thin stillage is diluted with an aqueous process liquid and fed to a further separation process, an aqueous phase is separated in this further separation process (the clear phase) containing and contains predominantly the dissolved dry matter, and the concentrated protein-rich phase is produced in this further separation process (the concentrate) and contains predominantly protein-rich suspended dry matter.

2. The method according to claim 1, characterised in that the mashing process is carried out with at least 0.25 kg thin stillage DM per kg of cereal DM.

3. The method according to claim 1, characterised in that a pH value<4.0 is maintained throughout the method.

4. The method according to claim 1, characterised in that a cold mashing process precedes the fermentation.

5. The method according to claim 1, characterised in that the solid-liquid separation of the whole stillage takes place in a filter press or in a decanter.

6. The method according to claim 1, characterised in that, by the partial recirculation to the mashing process, the raw protein content of the thin stillage is increased by at least 5% rel. compared to the raw protein content of the cereal less starch.

7. The method according to claim 1, characterised in that the partial dilution of the thin stillage is carried out with a process liquid, such as condensate selected from the group consisting of condensates from a thin stillage evaporation, condensates from a drying process, and lutter water from the distillation process and water.

8. The method according to claim 1, characterised in that the thin stillage is diluted with a process liquid in a ratio of at least 1:1 before the further separation in e).

9. The method according to claim 1, characterised in that the further separation of the diluted thin stillage into the clear phase and the concentrate is performed with the aid of a separator and takes place at least at 2800×g.

10. The method according to claim 1, characterised in that, by a targeted use of enzymes selected from the group of cellulases, hemicellulases, trehalases, xylanases, amylases, lipases, phytases and combinations thereof, non-protein-containing suspended substances are cleaved and dissolved.

11. The method according to claim 1, characterised in that the concentrate has a raw protein content increased by at least 15% rel. compared to the thin stillage.

12. The method according to claim 1, characterised in that the concentrate has a raw protein content of at least 44% DM.

13. The method according to claim 1, characterised in that the clear phase is at least partially returned to the process.

14. The method according to claim 1, characterised in that the concentrate is at least partially used directly as a high-quality protein feed or is fed to further treatment steps.

15. The method of claim 2, characterised in that the mashing process is carried out with at least 0.35 kg thin stillage DM per kg of cereal DM.

* * * * *

UNITED STATES PATENT AND TRADEMARK OFFICE
CERTIFICATE OF CORRECTION

PATENT NO. : 11,485,990 B2
APPLICATION NO. : 16/912562
DATED : November 1, 2022
INVENTOR(S) : Julia Pohl et al.

Page 1 of 1

It is certified that error appears in the above-identified patent and that said Letters Patent is hereby corrected as shown below:

In the Claims

Column 14, Line 4, Claim 1    Before "and" delete "containing"

Column 14, Line 26, Claim 7   Delete "liquid, such as condensate" and Insert -- liquid --

Signed and Sealed this
Eleventh Day of July, 2023

Katherine Kelly Vidal
*Director of the United States Patent and Trademark Office*